United States Patent [19]

Berry et al.

[11] Patent Number: 5,043,051
[45] Date of Patent: Aug. 27, 1991

[54] VARIABLE WIDTH ELECTROPHORESIS DEVICE

[76] Inventors: Nicole G. Berry; Robert R. Hellman, Jr., both of Eastman Kodak Co., Rochester, N.Y. 14650-2201

[21] Appl. No.: 534,578

[22] Filed: Jun. 6, 1990

[51] Int. Cl.⁵ .................. G01N 27/26; B01D 57/06
[52] U.S. Cl. ....................... 204/299 R; 204/182.8
[58] Field of Search ...................... 204/182.8, 299 R

[56] References Cited

U.S. PATENT DOCUMENTS 4,518,476  5/1985  Delony et al. .............. 204/182.8
4,828,669  5/1989  Hellman, Jr. ............... 204/299

OTHER PUBLICATIONS

Biorad Product Catalog, p. 152 (Mar., 1989).

*Primary Examiner*—T. Tung
*Assistant Examiner*—David G. Ryser

[57] ABSTRACT

There is described an electrophoresis device providing a support for a gel plate assembly, such support being improved in that it has means for varying the width of the support between at least two different values, using the said same support. Such means allows width variation to occur without dismantling the support.

7 Claims, 5 Drawing Sheets

VARIABLE WIDTH ELECTROPHORESIS DEVICE

FIELD OF THE INVENTION

This invention relates to an electrophoresis device and particularly to the support it provides to a gel plate assembly.

BACKGROUND OF THE INVENTION

In the field of electrophoresis, the sequencer device described in U.S. Pat. No. 4,828,669 represents a marked improvement in devices providing for such processing of proteins and nucleic acids. Such a device comprises at least one support for a gel plate assembly, and at least one buffer tank in liquid communication with the plate assembly. Most preferably, the support comprises a pair of fixed rails of fixed width, the buffer tank(s) being constructed to fit around the end(s) of the rails. As shown in the aforesaid patent, the rails are preferably inclined slightly from the vertical, to provide a resting surface for the plate assembly while it is being mounted on the support.

Although the above-mentioned device represents a marked improvement, it has one minor drawback—the width of the support as determined by the spacing of the fixed rails is fixed. This feature has in fact been standard on other electrophoresis devices as well. Gel plate assemblies come in a variety of widths, depending upon the number of sample lanes that are run within the gel. As a result, each electrophoresis device is usually dedicated to a fixed width, so that separate devices need to be constructed to accommodate differing widths of the gel plate assemblies.

More recently, an electrophoresis device has been described that allows for some width flexibility. The device, described on page 152 of the 1989 product catalog of BIORAD Laboratories as "Sequi-Gen Nucleic Acid Sequencing System", p. 152-154, allows a single base and lower buffer tank to be used with gel plate assemblies of two different widths, namely 21 cm and 38 cm. However, this device requires complete disassembly and reassembly to change the width size. That is, the entire gel plate support including the upper buffer tank is taken down and out of a "universal base" that provides the lower buffer tank, and a different gel plate support, gel plate assembly, and upper buffer tank is reassembled and inserted into that same base. Such variation in width is tedious and time-consuming, and requires different supports as well as a different upper buffer tank for each width, such tank being a fixed part of any given gel plate assembly.

Therefore, there has been a need prior to this invention to provide for a variable width electrophoresis device that accommodates variable widths of plates without requiring complete reassembly.

SUMMARY OF THE INVENTION

We have constructed an electrophoresis device that solves the above-noted problems.

More specifically, there is provided an electrophoresis device for electrophoretically separating charged compounds, the device comprising at least one support for mounting at least one gel plate assembly, and a buffer tank mounted for liquid communication with a gel plate assembly mounted on the support. The device is improved in that the support includes adjusting means for varying the width of said support between at least two different values to accommodate at least two different widths of gel plate assembly, using, however, the same said support.

Accordingly, it is an advantageous feature of the invention that the same electrophoresis device is useful for a variety of widths (and lengths) of gel plate assemblies, rather than for a single dedicated width; and without having to reassemble the support of the gel plate assembly.

It is a related advantageous feature of the invention that the electrophoresis device can be modified in its useful gel-plate width by the simple turn of a handle.

Other advantageous features will become apparent by reference to the following Description of the Preferred Embodiments, when read in light of the attached drawings.

DESCRIPTION OF THE PREFERRED EMBODIMENTS

The invention is described hereinafter with respect to the preferred embodiments, wherein the electrophoresis device has certain features including removable top and bottom buffer tanks and a gel plate assembly support that is inclined from the vertical. In addition, the invention of variable width is useful with any electrophoresis device, whether or not it has removable buffer tanks and regardless of the number of such tanks, and whether or not the support is inclined from the vertical.

Figure 1:
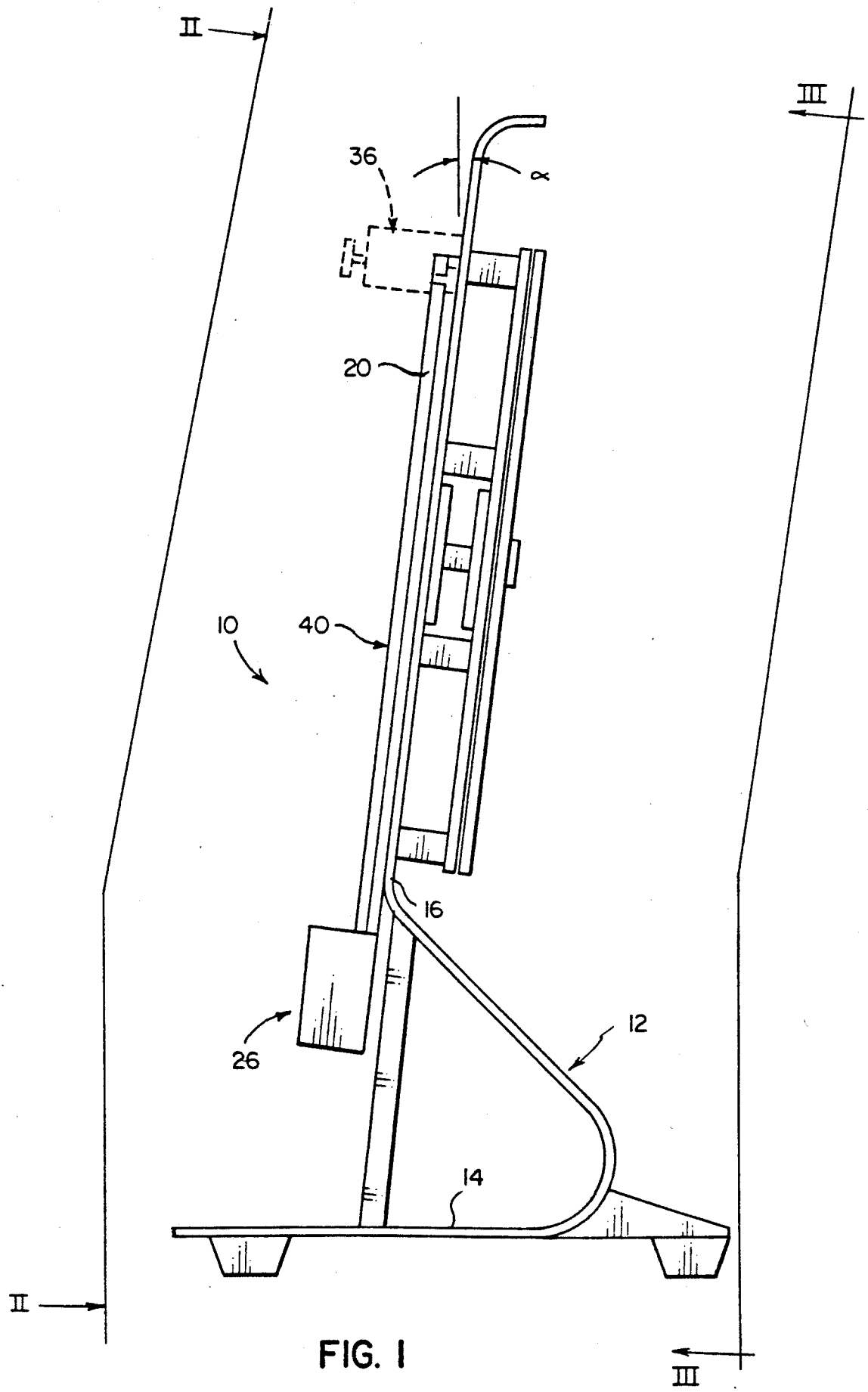
FIG. 1 is a side elevational view of an electrophoresis device constructed in accord with the invention.
Figure 4:
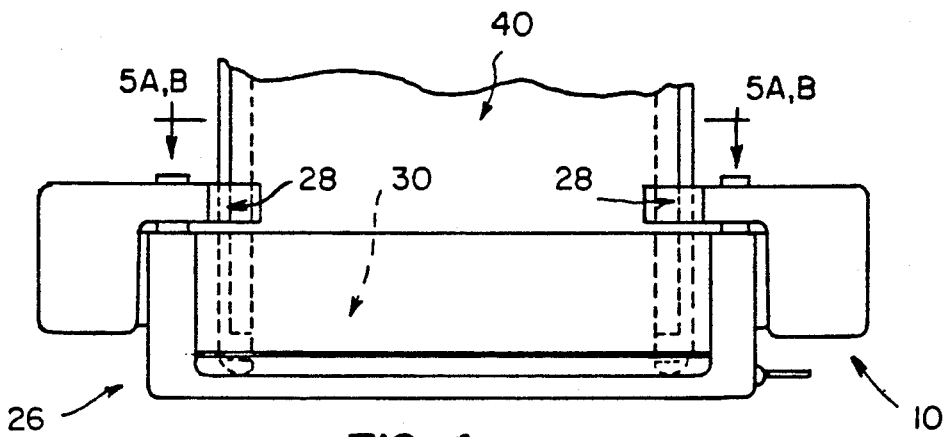
FIG. 4 is a fragmentary front elevational view illustrating a bottom buffer tank mounted on the device.

Referring to FIG. 1, an electrophoresis device 10 is constructed to have a frame support 12 which in turn has a base 14 and a rising back frame 16 tilted preferably at an angle alpha of from about 5° to about 10° from the vertical. As described in U.S. Pat. No. 4,828,669, this angle allows a gel plate assembly 40 to be assembled simply by leaning it against its supports. Those supports in turn comprise a pair of rails 20, 22 that extend generally parallel to each other, FIG. 2. Rails 20 and 22 are mounted for sliding movement towards and away from each other on back frame 16, as described hereinafter. A lower buffer tank 26 is mounted on plate assembly 40 with the latter immersed, FIGS. 1 and 4, and an upper buffer tank 36 is mounted at the upper end, FIG. 1.

Figure 5A:
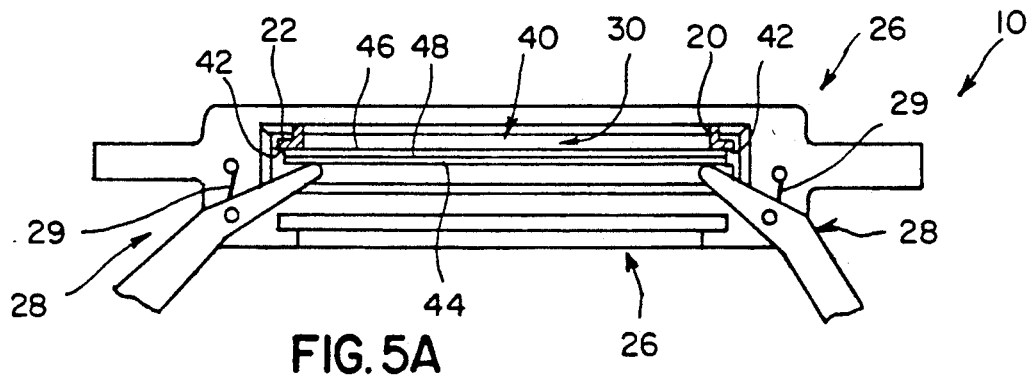
FIG. 5A is a section view taken generally along the line 5A—5A of FIG. 4.

Both the lower and upper buffer tanks are constructed and mounted substantially as described for U.S. Pat. No. 4,828,669—that is, they clamp onto the front of the gel plate assembly 40 by clamping against rails 20 and 22. Accordingly, few details need be described here. Clamps 28 are spring biased, 29, FIG. 5A, to press gel plate assembly 40 against rails 20 and 22, which are inserted into the box portion 30 of buffer tank 26.

Figure 2:
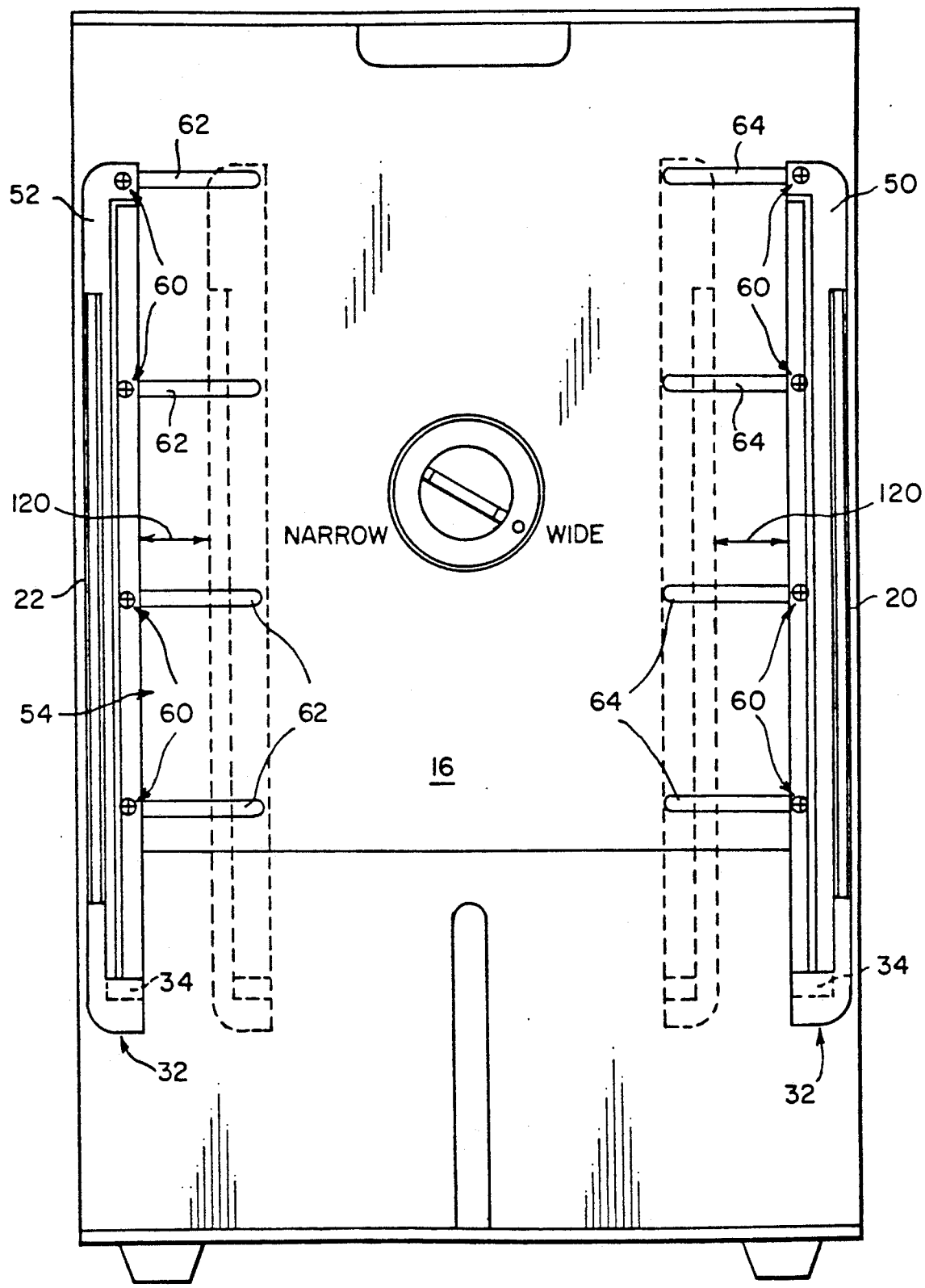
FIGS. 2 and 3 are a front and a rear elevational view of the device, taken along the lines II—II and III—III of FIG. 1, respectively, the buffer tanks and gel plate assembly having been removed for clarity.

Rails 20 and 22, FIG. 2, preferably have a bottom shoulder 32 constructed as described in U.S. Pat. No. 4,828,669 (FIG. 7) to hold gel plate assembly 40. Shoulder 32 provides a front surface 34 that protrudes in front of plate assembly 40 to create a pocket that holds and supports the bottom edge 38 of that assembly 40.

The rails can have any convenient cross-sectional shape. An L-shape is preferred, FIG. 5A, wherein the front leg 42 of the rail provides a front surface for contact and support of gel plate assembly 40. The opposite, rear surface of leg 42 is used for the clamp that holds upper buffer tank 36 in place (not shown), as is known from the aforesaid '669 patent.

Any convenient gel plate assembly can be used, which, as a minimum, provides a front glass sheet 44, a rear glass sheet 46, a spacer between them at the outside edges (not shown), and a gel 48 coated between the sheets. Preferably, a thermally-conducting sheet, such as a metal plate, is applied (not shown) to the back of sheet 46 to allow for better distribution of heat that builds up in the gel.

In accord with one aspect of the invention, means are provided for varying the width of the support, that is, of the spacing between rails 20 and 22, while still using the same rails. Indeed, the construction is such as to allow adjustment in the width without dismantling the rails, unlike the prior art device.

Figure 3:
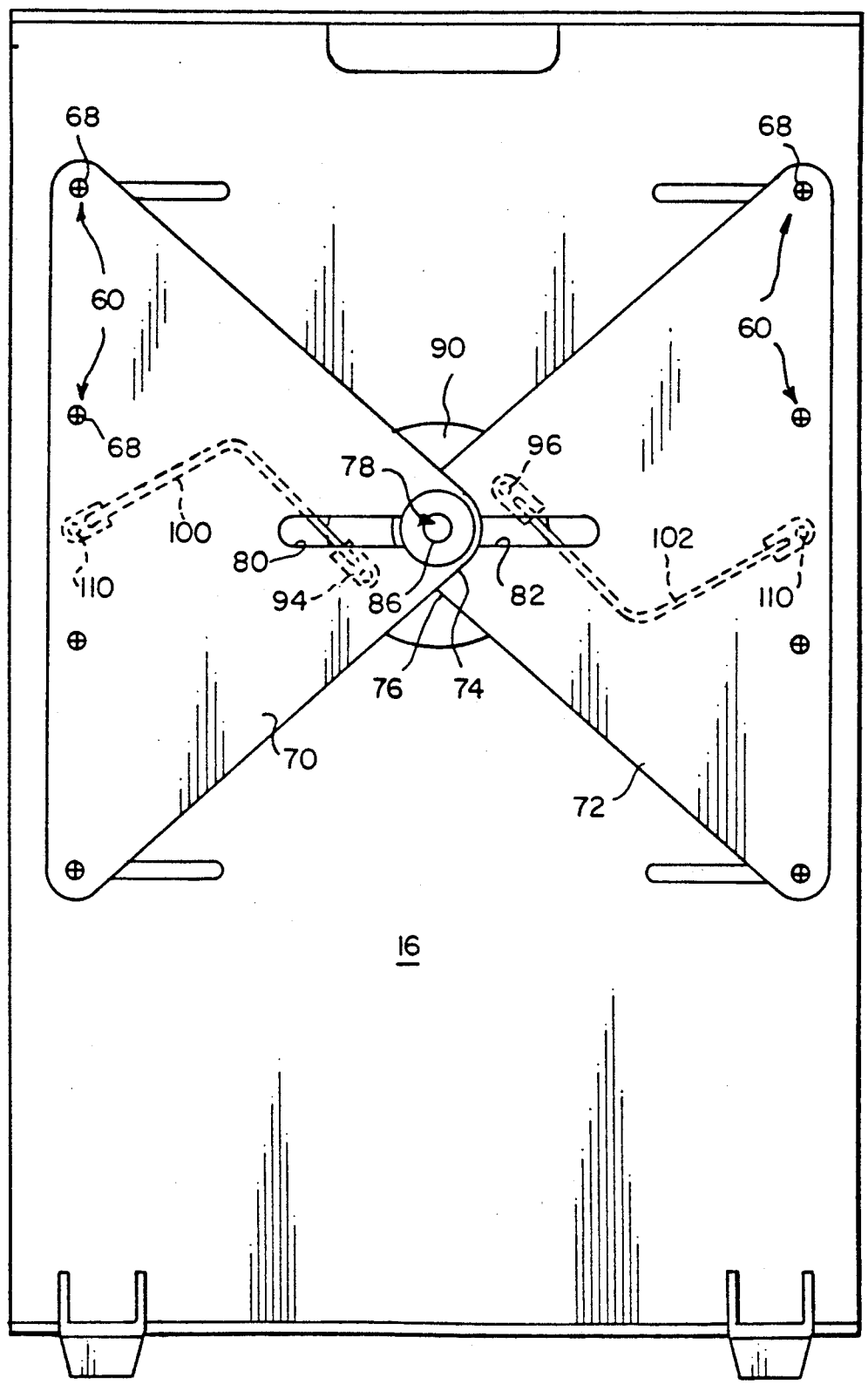

Referring to FIGS. 2 and 3, rails 20 and 22 are carried by elongated holders 50 and 52, which slide across the front surface 54 of frame 16. Holders 50 and 52 in turn have studs or screws 60 projecting rearwardly from the holders, through horizontally extending slots 62, 64, in frame 16. Those slots are spaced vertically along frame 16, and extend only a fraction of the width of frame 16. The opposite ends 68 of screws or studs 60 are affixed to two separate control plates 70, 72, FIG. 3, so that frame 16 is sandwiched between holders 50, 52 and plates 70, 72.

The control plates 70, 72 preferably overlap at their corners 74, 76, which overly the general center 78 of frame 16. Horizontal slots 80, 82 extend partway from corners 74 and 76 and in turn overlap each other. Slots 80 and 82 allow control plates 70 and 72 to slide past a control shaft 86 that is rotatably mounted at center 78. Attached to shaft 86 behind frame 16 is a drive member disc 90, and to shaft 86 in front of frame 16, FIG. 2, a handle 92. Drive disc 90 has mounted to it, FIG. 3, at off-center locations 94 and 96, two drive members in the form of flexible rods 100 and 102. One end of each of rods 100 and 102 is affixed to disc 90 at locations 94 and 96, and the other end 110 of each rod is operatively connected to a rail 20 or 22, respectively, by reason of its attachment to control plate 70 or 72.

No particular shape is critical to either disc 90 or handle 92, although a generally circular shape is preferred.

Figure 5B:
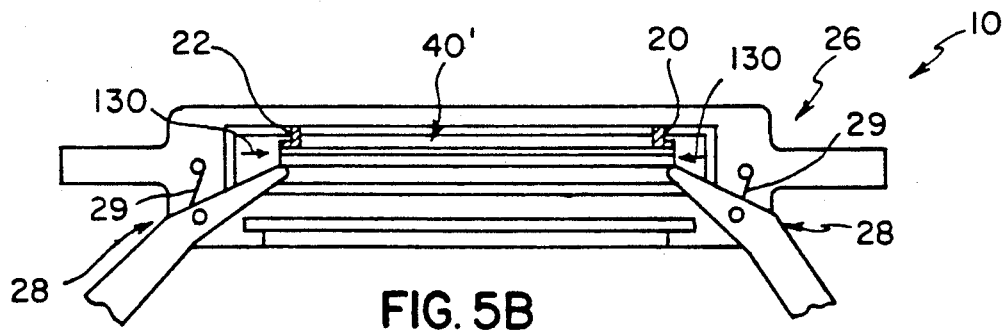
FIG. 5B is a section view similar to FIG. 5A, but with the support adjusted to a different width.

The operation of the width-varying means will be readily apparent from the preceding: Manual rotation of handle 92, FIG. 2, causes rotation of disc 90, FIG. 3, to bring ends 94 and 96 of rods 100 and 102 either closer to center 78, or to push them farther away from the center. If they are drawn closer together, plates 70 and 72, as well as the attached holders 50, 52, (FIG. 2) and the mounted rails 20, 22 also move closer together, arrows 120. In this fashion, the width of the support is changed from its maximum value, shown in solid lines, FIG. 2, to a lesser value and eventually to the minimum width, shown in phantom. Any width in between can be selected as well, producing an infinite width variation between these two limits. A maximum width gel plate assembly 40 is illustrated in place with buffer tank 26, FIG. 5A, whereas a minimum width gel plate assembly 40 is illustrated with the same buffer tank 26, FIG. 5B. The change occurs, arrows 130, without once removing the gel plate support (rails 20 or 22) from device 10.

Thus, useful widths of gel plate assembly 40 can include 21 and 38 cm, and any variation in between, for example.

Figure 6:
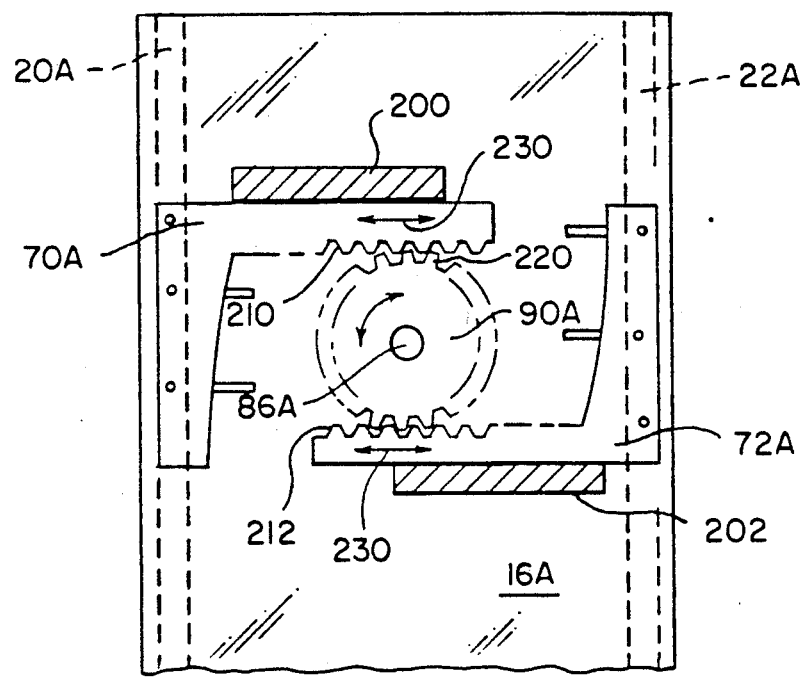
FIG. 6 is a fragmentary, partially schematic rear elevational view illustrating an alternate construction of the adjusting means for varying the width of the support.

Other drive and control mechanisms are equally useful in varying the spacing of rails 20 and 22, FIG. 6 being but one example. Parts similar to those previously described bear the same reference numeral, to which the distinguishing suffix "A" is appended.

Thus, device 10A is constructed exactly as described above, so that rails 20A and 22A are connected, via their holders and studs (not shown) to control plates 70A and 72A, driven by control disc 90A mounted on shaft 86A, as before. However, in this embodiment control plates 70A and 72A are generally rectangular and have no slots. Instead, they slide between backing members 200, 202 affixed to frame 16A. Also, the flexible rods are replaced by a rack gear 210, 212 on each of plates 70A and 72A, that engage a pinion gear 220 on disk 90A. Rotation of disc 90A produces a longitudinal movement, arrows 230, of control plates 70A, 72A to achieve movement of rails 20A and 22A, for width variation.

The invention has been described in detail with particular reference to preferred embodiments thereof, but it will be understood that variations and modifications can be effected within the spirit and scope of the invention.

What is claimed is:

1. In an electrophoresis device for electrophoretically separating charged compounds, the device comprising at least one support for mounting at least one gel plate assembly, said support having width-defining edges, and a buffer tank mounted and constructed to receive a gel plate assembly mounted on said support;

the improvement wherein said support includes adjusting means for varying the width of said support between at least two different values to accommodate at least two different widths of gel plate assembly using the same said support, said adjusting means including a manual control member mounted for rotation, and moving means responsive to rotation of said control member for automatically moving said support edges relative to each other between said two widths.

2. A device as defined in claim 1, wherein said adjusting means are constructed to provide an infinite variety of widths between a maximum and a minimum, without requiring said support to be dismounted from said device.

3. A device as defined in claims 1 or 2, wherein said edges include two opposed rails each being slidably mounted relative to each other.

4. A device as defined in claim 3, wherein each of said rails includes at one end a pocket constructed to fit around the side edge and front edge of a gel plate assembly, whereby said pocket is adjustable to receive said at least two different gel plate assemblies.

5. A device as defined in claim 3, wherein said manual control member comprises a handle and further including means for rotatably mounting said control member between said rails to pivot about an axis on said device, and a drive member for each of said rails, said drive member having opposite ends one of which is operatively secured to its rail and the other of which operatively engages said control member at a location off said axis, so that rotation of said rotatable member moves each of said drive members and its respective rail closer to or farther from said axis, and thus from the opposite rail.

6. A device as defined in claim 5, wherein said other end of said drive member is eccentrically attached to said rotatable control member.

7. A device as defined in claim 5, wherein said control member includes a pinion gear and said drive members each include a rack confined to engage said pinion gear.

* * * * *